United States Patent [19]

Enokida et al.

[11] Patent Number: 5,698,740
[45] Date of Patent: Dec. 16, 1997

[54] HOLE-TRANSPORT MATERIAL

[75] Inventors: Toshio Enokida; Tadashi Ogawa; Yasumasa Suda, all of Tokyo, Japan

[73] Assignee: Toyo Ink Manufacturing Co., Ltd., Tokyo, Japan

[21] Appl. No.: 800,211

[22] Filed: Feb. 12, 1997

Related U.S. Application Data

[62] Division of Ser. No. 313,880, Sep. 28, 1994, abandoned.

[30] Foreign Application Priority Data

Oct. 1, 1993 [JP] Japan ................. 5-246551

[51] Int. Cl.$^6$ ................. C07C 211/54
[52] U.S. Cl. ................. 564/308; 548/193; 548/156; 548/440; 549/59; 558/420; 560/251
[58] Field of Search ................. 564/308; 549/59; 558/420; 560/251

[56] References Cited

U.S. PATENT DOCUMENTS

| 4,720,432 | 1/1988 | Van Slyke et al. | 428/457 |
| 5,061,569 | 10/1991 | Van Slyke et al. | 428/457 |
| 5,420,288 | 5/1995 | Ohta et al. | 548/145 |

FOREIGN PATENT DOCUMENTS

| 6-65569 | 3/1994 | Japan . |
| 6-220437 | 8/1994 | Japan . |

OTHER PUBLICATIONS

M. Watanabe et al., Mem. Fac. Eng., Osaka City Univ., vol. 34, pp. 17–24 (1993).

*Primary Examiner*—Richard L. Raymond
*Attorney, Agent, or Firm*—Wenderoth, Lind & Ponack

[57] ABSTRACT

A hole-transport material having excellent hole-transport capability and durability, suitable for use in an organic EL device and as an organic photoconductive material, has the formula (1).

4 Claims, 4 Drawing Sheets

HOLE-TRANSPORT MATERIAL

This application is a divisional application of now abandoned Ser. No. 08/313,880 filed Sep. 28, 1994, now abandoned.

FIELD OF THE INVENTION

The present invention relates to a hole-transport material having a fluorene structure, which can be used as a photosensitive material or an organic photoconductive material. More specifically, it relates to a hole-transport material, which is suitable for use as an organic photoconductive material for an organic electroluminescence (to be referred to as EL hereinafter) device used as a plane light source, an electrophotographic photoreceptor, a photoelectric converter and a solar cell.

PRIOR ART OF THE INVENTION

Organic photoconductive materials developed as photosensitive materials or hole-transport materials are advantageous in many respects. That is, they are inexpensive, versatilely processable and free from causing harm to the public. A variety of compounds as organic photoconductive materials have been proposed. For example, there have been disclosed organic photoconductive materials such as oxadiazole derivatives (U.S. Pat. No. 3,189,447), oxasole derivatives (U.S. Pat. No. 3,257,203), hydrazone derivatives (U.S. Pat. No. 3,717,462, JP-A-54-59,143 and U.S. Pat. No. 4,150,978), triazole pyrazoline derivatives (U.S. Pat. No. 3,820,989, JP-A-51-93,224, JP-A-51-93,224 and JP-A-55-108,667), arylamine derivatives (U.S. Pat. No. 3,180,730, U.S. Pat. No. 4,232,103, JP-A-55-144,250 and JP-A-56-119,132) and stilbene derivatives (JP-A-58-190,953 and JP-A-59-195,658).

An organic EL device is one of products produced by a technique using a hole-transport material. An EL device using an organic material is expected to be useful as a solid emission type, inexpensive and large-area full color display device, and developed in various ways. Generally, an EL device is formed of a light-emitting layer and a pair of opposing electrodes between which the light-emitting layer is sandwiched. The light emission takes place as follows. When an electric field is applied between a pair of the electrodes, the light-emitting layer is implanted with electrons from the cathode, and is implanted with holes from the anode. Further, the electrons recombine with the holes in the light-emitting layer, and energy is released as light when the energy level of the electrons is shifted from a conduction band to a valence band.

Conventional organic EL devices require high actuation voltage and show low light emission brightness and low light emission efficiency when compared with inorganic EL devices. Further, conventional EL devices extraordinarily deteriorate in properties, and have not yet been sufficient for practical use.

In recent years, there has been reported an organic EL device which emits light at a low voltage of less than 10V and is fabricated by laminating a thin film containing an organic compound having a high fluorescence quantum efficiency, and the device attracts attention (Applied Physics Letters, Vol. 51, page 913, 1987).

The above organic EL device, being formed of a metal chelate complex as a fluorescent material layer and an amine compound as a hole-injecting layer, gives green light emission at a high brightness, and has performances almost adequate for practical use. That is, when a direct current of 6 or 7V is applied, the device accomplishes a brightness of $100/m^2$ cd and a maximum light emission efficiency of 1.5 lm/W.

Conventional organic EL devices including the above EL device have improved light emission strength due to improvements in constitution, while they have no sufficient light emission brightness. Further, the major problem with them is that they are poor in stability when used repeatedly. It is therefore desired to develop a hole-transport material having excellent hole-transport capability and sufficient durability for developing an organic EL device having a higher light emission brightness and excellent stability in repeated use.

An electrophotographic photoreceptor is another product produced by a technique using a hole-transport material. The electrophotography is one of imaging methods, which was invented by Carlson. In this method, an electrophotographic photoreceptor is charged by corona discharge and then imagewise exposed to light to obtain a static latent image, the latent image is developed by attaching a toner to the latent image, and an image of the toner is transferred to a receptor. The electrophotographic photoreceptor is basically required to have the following properties; A proper potential is retained in a dark place, discharging in a dark place hardly takes place, and discharging readily occurs under the irradiation with light. The electrophotographic photoreceptor is conventionally formed from an inorganic photoconductor such as selenium, a selenium alloy, zinc oxide, cadmium sulfide or tellurium. The problems pointed out concerning these photoconductors are that they are poor in processability and toxic. For overcoming these problems, the development of an organic electrophotographic photoreceptor is under way. At present, however, electrophotographic photoreceptors using conventional organic photoconducting materials as hole-transport materials are not necessarily satisfactory in electrophotographic properties such as chargeability, sensitivity and residual potential. It is therefore desired to develop a hole-transport material having excellent charge-transport capability and durability.

SUMMARY OF THE INVENTION

It is an object of the present invention to provide a hole-transport material having excellent hole-transport capability and durability.

It is another object of the present invention to provide an organic EL device or a device for an electrophotographic photoreceptor, which are excellent in sensitivity and stability in repeated use.

It is further another object of the present invention to provide a hole-transport material suitable for use as an organic photoconductive material.

According to the present invention, there is provided a hole-transport material of the formula (1), (I)

wherein each of $R^1$ to $R^{18}$ is independently a hydrogen atom, a halogen atom, an alkyl group, a substituted alkyl group, an alkoxy group, a substituted alkoxy group, a thioalkoxy group, a substituted thioalkoxy group, a cyano group, an amino group, a mono- or disubstituted amino group, a hydroxyl group, a mercapto group, an aryloxy group, a substituted aryloxy group, an arylthio group, a substituted arylthio group, a carbocyclic aromatic group, a substituted carbocyclic aromatic group, a heterocyclic aromatic group, a substituted heterocyclic aromatic group, a heterocyclic group or a substituted heterocyclic group, and any neighboring substituents may form an aliphatic cyclic group, a substituted aliphatic cyclic group, a carbocyclic aromatic group, a substituted carbocyclic aromatic group, a heterocyclic aromatic group, a substituted heterocyclic aromatic group, a heterocyclic group or a substituted heterocyclic group, provided that at least one of $R^9$ to $R^{13}$ is an amino group or a mono- or disubstituted amino group and that at least one of $R^{14}$ to $R^{18}$ is an amino group or a mono- or disubstituted amino group.

According to the present invention, there is also provided an organic EL device comprising a pair of electrodes and a light-emitting layer sandwiched between the electrodes and formed of one or a plurality of thin films of an organic compound, wherein at least one of the thin films contains the hole-transport material of the present invention.

According to the present invention, further, there is provided an organic EL device comprising a pair of electrodes, a light-emitting layer formed of one or a plurality of thin films of an organic compound and a hole-injecting layer formed of one or a plurality of thin films of an organic compound, the light-emitting layer and the hole-injecting layer being sandwiched between the electrodes, wherein at least one of the thin films of an organic compound contains the hole-transport material of the present invention.

According to the present invention, further, there is provided an electrophotographic photoreceptor formed by providing a charge-generating material and a hole-transport material onto an electrically conductive support, the hole-transport material being the hole-transport material of the present invention.

DETAILED DESCRIPTION OF THE INVENTION

In order to overcome the above problems, the present inventors have made diligent studies and found that the hole-transport material of the following formula (1) has the high capability of hole-transport and that an organic EL device and a device of an electrophotographic photoreceptor using the hole-transport material of the formula (1) are excellent in sensitivity and stability in repeated use.

(I)

In the formula (1), each of $R^1$ to $R^{18}$ is independently a hydrogen atom, a halogen atom, an alkyl group, a substituted alkyl group, an alkoxy group, a substituted alkoxy group, a thioalkoxy group, a substituted thioalkoxy group, a cyano group, an amino group, a mono- or disubstituted amino group, a hydroxyl group, a mercapto group, an aryloxy group, a substituted aryloxy group, an arylthio group, a substituted arylthio group, a carbocyclic aromatic group, a substituted carbocyclic aromatic group, a heterocyclic aromatic group, a substituted heterocyclic aromatic group, a heterocyclic group or a substituted heterocyclic group, and any neighboring substituents may form an aliphatic cyclic group, a substituted aliphatic cyclic group, a carbocyclic aromatic group, a substituted carbocyclic aromatic group, a heterocyclic aromatic group, a substituted heterocyclic aromatic group, a heterocyclic group or a substituted heterocyclic group, provided that at least one of $R^9$ to $R^{13}$ is an amino group or a mono- or disubstituted amino group and that at least one of $R^{14}$ to $R^{18}$ is an amino group or a mono- or disubstituted amino group.

The above halogen atom includes fluorine, chlorine, bromine and iodine.

The above alkyl group and substituted alkyl group include methyl, ethyl, propyl, butyl, sec-butyl, tert-butyl, pentyl, hexyl, heptyl, octyl, stearyl, trichloromethyl, cyclopropyl, cyclohexyl, 1,3-cyclohexadienyl, 2-cyclopenten-1-yl and 2,4-cyclopentadien-1-ylidenyl.

The above alkoxy group and substituted alkoxy group include methoxy, ethoxy, propoxy, n-butoxy, sec-butoxy, tert-butoxy, pentyloxy, hexyloxy and stearyloxy.

The above thioalkoxy group and substituted thioalkoxy group include methylthio, ethylthio, propylthio, butylthio, sec-butylthio, tert-butylthio, pentylthio, hexylthio, heptylthio and octylthio.

The monosubstituted amino group and disubstituted amino group include methylamino, dimethylamino, ethylamino, diethylamino, dipropylamino, dibutylamino, diphenylamino, bis(acetoxymethyl)amino, bis(acetoxyethyl)amino, bis(acetoxypropyl)amino, bis(acetoxybutyl)amino and dibenzylamino.

The aryloxy group and substituted aryloxy group include phenoxy, p-tert-butylphenoxy and 3-fluorophenoxy.

The arylthio group and substituted arylthio group include phenylthio and 3-fluorophenylthio.

The carbocyclic aromatic group and substituted carbocyclic aromatic group include phenyl, biphenylenyl, triphenylenyl, tetraphenylenyl, 3-nitrophenyl, 4-methylthiophenyl, 3,5-dicyanophenyl, o-, m- and p-tolyl, xylyl, o-, m- and p-cumenyl, mesityl, pentalenyl, indenyl, naphthyl, azulenyl, heptalenyl, acetonaphthalenyl, phenalenyl, fluorenyl, anthryl, anthraquinonyl, 3-methylanthryl, phenanthryl, triphenylenyl, pyrenyl, chrysenyl, 2-ethyl-1-chrysenyl, picenyl, perylenyl, 6-chloroperylenyl, pentaphenyl, pentacenyl, tetraphenylenyl, hexaphenyl, hexacenyl, rubicenyl, coronenyl, trinaphthylenyl, heptaphenyl, heptacenyl, pyranthrenyl and ovalenyl.

The heterocyclic aromatic group and substituted heterocyclic aromatic group include thionyl, furyl, pyrrolyl, imidazolyl, pyrazolyl, pyridyl, piperazinyl, pyrimidinyl, pyridazinyl, indolyl, quinolyl, isoquinolyl, phthalazinyl, quinoxalinyl, quinazolinyl, carbazolyl, acridinyl, phenazinyl, furfuryl, isothiazolyl, furazanyl, phenoxazinyl, benzothiazolyl, benzoxazolyl, benzimidazolyl, 2-methylpyridyl and 3-cyanopyridyl.

At least one of $R^9$ to $R^{13}$ is an amino group or a mono- or disubstituted amino group, and at least one of $R^{14}$ to $R^{18}$ is an amino group or a mono- or disubstituted amino group. The substituent on the amino group may be any one of those substituents which are included in $R^1$ to $R^{18}$. Although not specially limited, specific examples of the substituent on the amino group preferably include alkyl and substituted alkyl groups such as methyl, ethyl, propyl and tert-butyl; carbocyclic aromatic and substituted carbocyclic aromatic groups such as phenyl, o-tolyl, m-tolyl, p-tolyl, p-chlorophenyl, p-methoxyphenyl and p-(N,N-diphenyl)aminophenyl; and heterocyclic and substituted heterocyclic groups such as pyridyl, pyrazinyl, pyrimidinyl, triazinyl and quinoxalinyl.

In the present invention, the compound of the formula (1) can be produced, e.g., by the following method.

The compound of the formula (1) can be obtained by reacting amino groups on the phenyl groups of the compound of the formula (1) with a derivative compound having a halogen, etc., as a substituent, under a nitrogen-containing atmosphere in the presence or absence of an organic solvent in the presence of a base and a catalyst at a predetermined temperature for a predetermined period of time.

The halogen as a substituent on the derivative compound used for the synthesis of the compound of the present invention include chlorine, bromine, iodine, which particularly easily replace the amino group. In the production of the compound of the formula (1), the base is selected from inorganic bases such as potassium carbonate, lithium hydroxide and sodium hydroxide and organic bases such as pyridine, picoline, triethylamine, N-methylpyrrolidine and 1,5-diazabicyclo[5,4,0]undecene (DBU). The solvent is selected from toluene, xylene, nitrobenzene, dimethylsulfoxide and N,N-dimethylformamide, if used. The acid catalyst is selected from concentrated sulfuric acid, p-toluenesulfonic acid, polyphosphoric acid, $TiCl_4$, $AlCl_3$ and polyethylenesulfonic acid. A reducing agent may be used, and it is selected from Zn, Sn, $H_2$/Pt, $H_2$/Pd and $H_2$/Ni.

Typical examples of the compound of the formula (1) are as follows.

| Compound | Chemical Structure |
|---|---|
| (1) | |
| (2) | |

-continued

| Compound | Chemical Structure |
|---|---|
| (3) | [structure: 2,7-dimethylfluorene with two 4-(N,N-di-p-tolylamino)phenyl groups at 9,9-position] |
| (4) | [structure: fluorene with two 4-[N,N-bis(4-methoxyphenyl)amino]phenyl groups at 9,9-position] |
| (5) | [structure: fluorene with two 4-(N,N-diphenylamino)phenyl groups at 9,9-position] |
| (6) | [structure: 2,7-dimethylfluorene with two 4-(N,N-diphenylamino)phenyl groups at 9,9-position] |

-continued

| Compound | Chemical Structure |
|---|---|
| (7) | 9,9'-spirobifluorene with two 4-(dimethylamino)phenyl substituents |
| (8) | 9,9'-spirobifluorene with two [4-(N-phenyl-N-(4-cyanophenyl)amino)phenyl] substituents |
| (9) | 9,9'-spirobifluorene with two [4-(N,N-di(o-tolyl)amino)phenyl] substituents |
| (10) | 9,9'-spirobifluorene with two [4-(N,N-dicyclohexylamino)phenyl] substituents |
| (11) | 9,9'-spirobifluorene with two [4-(N,N-di(2-thienyl)amino)phenyl] substituents |

-continued

| Compound | Chemical Structure |
|---|---|
| (12) | |
| (13) | |
| (14) | |
| (15) | |

The hole-transport material of the present invention may be used as a mixture with other hole-transport or electron-transport material. The hole-transport material of the present invention is excellent in hole-transport capability, and can be used very effectively as such.

First, the use of the compound of the formula (1) as a hole-transport material for an organic EL device will be explained hereinafter. The compound of the formula (1) can be used as a hole-transport material in any one of a hole-injecting layer and a light-emitting layer.

Figure 1:
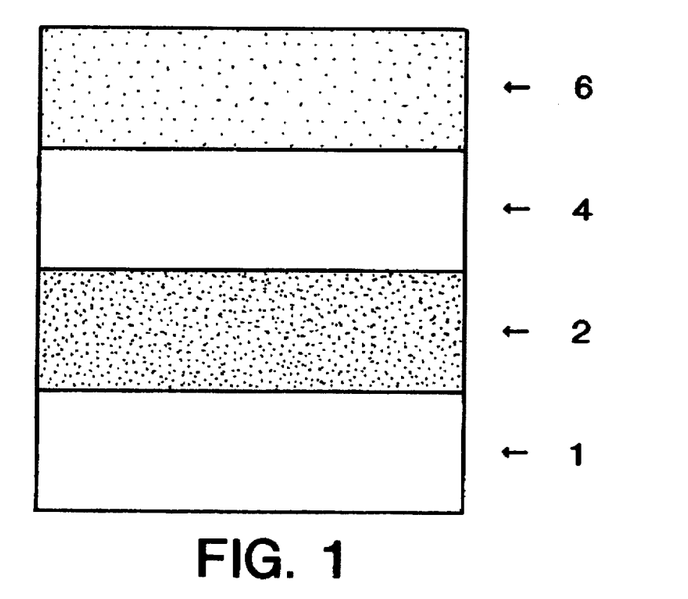
FIG. 1 is a schematic cross-sectional view of an organic EL device used in Examples.
Figure 2:
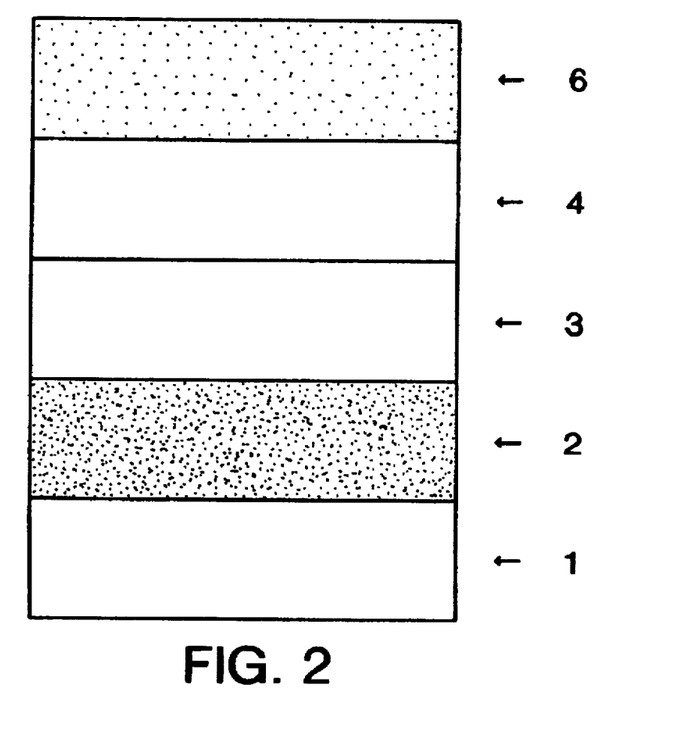
FIG. 2 is a schematic cross-sectional view of an organic EL device used in Examples.
Figure 3:
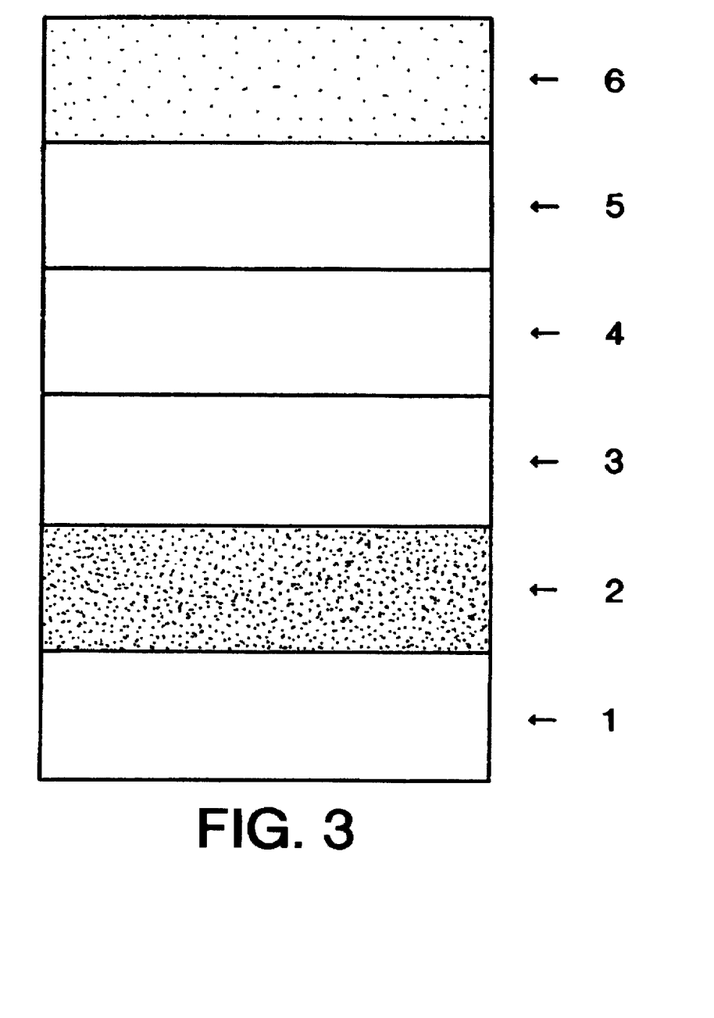
FIG. 3 is a schematic cross-sectional view of an organic EL device used in Examples.

FIGS. 1 to 3 schematically show organic EL devices, in which an electrode A is an anode and an electrode B is a cathode.

FIG. 1 shows an organic EL device having a structure in which a substrate 1, an electrode A (anode) indicated by numeral 2, a light-emitting layer 4 and an electrode B (cathode) indicated by numeral 6 are consecutively laminated. The light-emitting layer 4 may contain, in addition to the compound of the formula (1), a light-emitting substance, a light-emitting auxiliary material, a hole-transport material or an electron-transport material. In the light-emitting layer 4, the compound of the formula (1) functions a hole-transport, light-emitting material. When other light-emitting substance is contained in the light-emitting layer 4, the compound of the formula (1) may be made to function as a hole-transport material.

FIG. 2 shows an organic EL device having a structure in which a substrate 1, an electrode A (anode) indicated by numeral 2, a hole-injecting layer 3, a light-emitting layer 4 and an electrode B (cathode) are consecutively laminated. In this organic EL device, the light-emitting layer 4 and the hole-injecting layer 3 are discretely provided. This discrete structure improves the efficiency of implanting holes from the hole-injecting layer 3 to the light-emitting layer 4, and the light emission brightness and light emission efficiency improve. The light-emitting substance used in the light-emitting layer 4 may be selected from materials having electron-transport capability, or the light-emitting layer 4 may be imparted with the capability of transporting electrons by incorporating an electron-transport material into the light-emitting layer 4, so that the light emission efficiency can be further improved. The compound of the formula (1) may be incorporated into the light-emitting layer 4 alone, the hole-injecting layer 3 alone or both of the light-emitting layer 4 and the hole-injecting layer 3.

FIG. 3 shows an organic EL device having a structure in which a substrate 1, an electrode A (anode) indicated by numeral 2, a hole-injecting layer 3, a light-emitting layer 4, an electron-injecting layer and an electrode B (cathode) indicated by numeral 6 are consecutively laminated. This organic EL device additionally has the hole-injecting layer 3 and the electron-injecting layer 5 as compared with the organic EL device shown in FIG. 1, so that the efficiency of recombination of holes and electrons in the light-emitting layer 4 is improved. The organic EL device is structured to have a multi-layered structure, so that decreasing of the brightness and decreasing of the device life can be prevented. Like the device shown in FIG. 2, the compound of the formula (1) can be incorporated into the light-emitting layer 4 alone, the hole-injecting layer 3 alone or both of the light-emitting layer 4 and the hole-injecting layer 3. In the organic EL devices shown in FIGS. 2 and 3, each light-emitting layer 4 may contain, in addition to the compound of the formula (1), a light-emitting substance, a light-emitting auxiliary material, a hole-transport material or an electron-transport material. Further, each of the hole-injecting layer, the light-emitting layer and the electron-injecting layer may be structured to have at least two layers.

The electrically conductive substance used in the anode in each organic EL device preferably has a work function of greater than 4 eV. That is, it is selected from carbon, aluminum, vanadium, iron, cobalt, nickel, tungsten, silver, gold, palladium, alloys of these, metal oxides such as tin oxide which is called an ITO substrate or an NESA substrate and indium oxide, and organic, electrically conductive resins such as polythiophene and polypyrrole.

The electrically conductive substance used in the cathode preferably has a work function of smaller than 4 eV. That is, it is selected from magnesium, calcium, tin, lead, titanium, yttrium, lithium, ruthenium, manganese and alloys of these, while the above substance shall not be limited to these. The anode and the cathode may be structured to have at least two layers.

In each organic EL device, at least one of the anode A indicated by numeral 2 and the electrode B indicated by numeral 6 is preferably fully transparent in the light emission wavelength region of the device. Further, the substrate 1 is also preferably transparent. The transparent electrode is produced from the above electrically conductive material by a vapor-deposition or sputtering method so that the electrode has a predetermined transparency. The electrode which constitutes a light emission surface preferably has a light transmittance of at least 10%.

The substrate 1 is not specially limited if it has mechanical and thermal strengths and transparency. For example, it is selected from a glass substrate and substrates of transparent resins such as polyethylene, polyether sulfone and polypropylene.

In the organic EL devices of the present invention, each layer may be formed by any one of dry film forming methods such as vacuum deposition and sputtering methods and wet film forming methods such as spin coating and dipping methods. The thickness of each layer is not specially limited, while the layers are formed to have proper thicknesses. When the thicknesses of the layers are too large, inefficiently, a high voltage is required for obtaining a predetermined optical output. When the thicknesses are too small, a pinhole is liable to occur, and the light emission brightness is liable to be insufficient even when an electric field is applied. The thicknesses of the layers are generally 5 nm to 10 μm, preferably 10 nm to 0.2 μm.

When each layer is formed by a wet film forming method, each layer is formed using a solution or dispersion of the corresponding material in a proper solvent such as chloroform, tetrahydrofuran or dioxane. For improving the film formability and preventing pinholes, etc., a proper resin and a proper additive may be incorporated into the solution or dispersion.

The above resin is selected from insulating resins such as polystyrene, polycarbonate, polyarylate, polyester, polyamide, polyurethane, polysulfone, polymethyl methacrylate, polymethyl acrylate and cellulose, photoconductive resins such as poly-N-vinylcarbazole and polysilane and electrically conductive resins such as polythiophene and polypyrrole.

In each organic EL device, the light-emitting layer and the hole-injecting layer may contain a known light-emitting substance, light-emitting auxiliary substance, hole-transport material and electron-transport material in addition to the compound of the formula (1).

The known light-emitting substance or light-emitting auxiliary substance includes anthracene, naphthalene, phenathorene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarin, oxadiazole, aldazine, bisbenzoxazoline, bisstyryl, pyrazine, cyclopentadiene, oxine, aminoquinoline, imine, diphenylethylene, vinylanthracene, diaminocarbozole, pyran, thiopyran, polymethine, merocyanine, an imidazole chelated oxinoide compound, quinacridone, rubrene and derivatives of these, while the above substance shall not be limited to these.

The hole-transport material which can be used in combination with the hole-transport material of the formula (1) is selected from compounds which have hole-transport capability, have an excellent effect of implanting the light-emitting layer or the light-emitting substance with holes, prevent the movement of excitons generated in the light-emitting layer to the electron-injecting layer or the electron-transport material, and have excellent thin-film formability. Specific examples of the above hole-transport material include phthalocyanine compounds, naphthalocyanine compounds, porphyrin compounds, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type tiphenylamine, styrylamine type triphenylamine, diamine type tiphenylamine, derivatives of these, polyvinylcarbazole, polysilane and polymer materials such as electrically conductive polymers, while the above hole-transport material shall not be limited to these.

The electron-transport material is selected from compounds which has the electron-transport capability, have an excellent effect of implanting the light-emitting layer or the light-emitting substance with electrons, prevent the movement of excitons generated in the light-emitting layer to the electron-injecting layer or the electron-transport material, and have excellent thin-film formability. The electron-transport material includes fluorenone, anthraquinodimethane, diphenoquinone, thiopyrandioxide, oxadiazole, perylene tetracarboxylic acid, fluorenylidenemethane, anthraquinodimethane, anthrone and derivatives of these, while the electron-transport material shall not be limited to these.

Further, the organic EL device can be further sensitized by incorporating an electron-receiving substance into the hole-transport material or incorporating an electron-donating substance into the electron-transport material.

In the organic EL devices of FIGS. 1 to 3, the compound of the formula (1) may be used in any one of the light-emitting layer and the hole-injecting layer. Further, the compound of the formula (1) may be used in combination with at least one of the light-emitting substance, the light-emitting auxiliary material, the hole-transport material and the electron-transport material.

Further, for improving the stability of the organic EL devices of the present invention against temperature, humidity and atmosphere, a protection layer may be provided on the surface of each device, and for protecting the device as a whole, a silicone oil may be sealed.

In the present invention, due to the use of the compound of the formula (1) for the organic EL devices, the light emission efficiency and the light emission brightness can be increased. Further, the devices are highly stable against heat and electric current, and the brightness feasible for practical use can be obtained at a low actuation voltage. As a result, the deterioration of the device, which has been a serious problem, can be decreased to a great extent.

The organic EL devices of the present invention have a high industrial value, since they can be applied to a flat panel display of a wall-hanging TV set and plane light-emitting devices such as a light source for a copying machine or a printer, a light source for a liquid crystal display or a meter, a display and a signing lamp.

The use of the compound of the formula (1) in an electrophotographic photoreceptor will be explained hereinafter.

Figure 4:
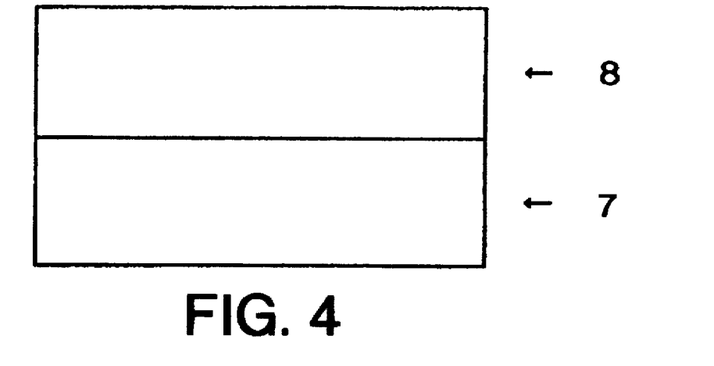
FIG. 4 is a schematic cross-sectional view of an electrophotographic photoreceptor used in Examples.
Figure 5:
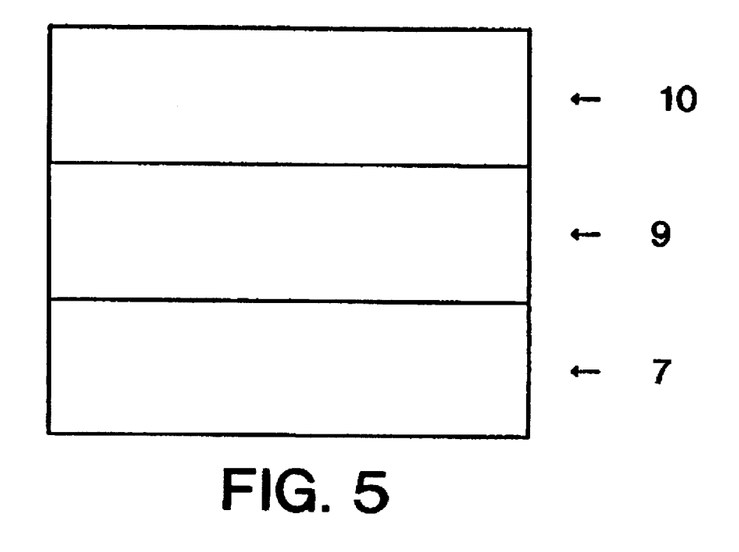
FIG. 5 is a schematic cross-sectional view of an electrophotographic photoreceptor used in Examples.

The electrophotographic photoreceptor includes a single-layered photoreceptor manufactured by forming a photosensitive layer 8 on an electrically conductive substrate 7 as shown in FIG. 4, the photosensitive layer 8 being formed from a dispersion of a charge-generating material and optionally a charge-transport material in a binder resin, and a laminated photoreceptor manufactured by consecutively laminating a charge-generating layer 9 and a hole-transport layer 10 on an electrically conductive substrate 7 as shown in FIG. 5. The charge-generating layer 9 and the hole-transport layer 10 may be laminated in the order adverse to that shown in FIG. 5. Further, the electrically conductive substrate 7 may have an undercoat layer (not shown) on the surface. The undercoat layer is provided for improving the electrophotographic properties and image properties by improving the adhesion and contact between the electrically conductive substrate and a layer formed thereon. Further, an overcoat layer may be provided as a top coat on the electrophotographic photoreceptor for protecting the photoreceptor surface from active gas and preventing the filming of a toner.

The compound of the formula (1) can be used in any one layer of the electrophotographic photoreceptor, while it is preferably used as a hole-transport material since it has the high hole-transporting capability. The compound of the formula (1) works as a hole-transport material, very effectively carries charges generated by the absorption of light, and gives a photoreceptor showing a response at a high rate. Further, the compound of the formula (1) is excellent in ozone resistance and optical stability, and gives a photoreceptor having excellent durability.

The charge-generating material is selected from organic compounds such as bisazo, quinacridone, diketopyrrolopyrrole, indigo, perylene, perinone, polycyclic quinone, squalirium salt, azulenium salt, phthalocyanine and naphthalocyanine, and inorganic materials such as selenium, selenium-tellurium alloy, cadmium sulfide, zinc oxide and amorphous silicon.

Each layer for the photoreceptor can be formed by any one of a vapor deposition method and a dispersion-applying method. The dispersion is applied with any one of a spin coater, an applicator, a spray coater, an immersion coater, a roll coater, a curtain coater and a bead coater, and the resultant coating is statically dried, or air-dried, at a temperature of from room temperature to 200° C. for 10 minutes to 6 hours. The thickness of the dry photosensitive layer in the single-layered photoreceptor is 5 to 50 µm. In the laminated photoreceptor, the thickness of the dry charge-generating layer is 0.01 to 5 µm, preferably 0.1 to 1 µm, and the thickness of the dry hole-transport layer is 5 to 50 µm, preferably 10 to 20 µm.

The resin optionally used for forming the photosensitive layer of the single-layered photoreceptor and the charge-generating layer or hole-transport layer of the laminated photoreceptor can be selected from a wide range of insulating resins. It can be also selected from organic photoconductive polymers such as poly-N-vinylcarbozole, polyvinylanthracene and polysilanes. The above resin is preferably selected from insulating resins such as polyvinyl butyral, polyarylate, polycarbonate, polyester, phenoxy, acryl, polyamide, urethane, epoxy, silicone, polystyrene, polyvinyl chloride, a vinyl chloride-vinyl acetate copolymer, phenol and a melamine resin. The amount of the resin optionally used for forming the charge-generating layer or the hole-transport layer is preferably 100% by weight or less of the amount of the charge-generating material or the hole-transport material. The above resins may be used in combination. Further, the charge-generating layer may be formed by a physical film forming methd such as a vapor deposition or sputtering method. The vapor deposition or sputtering is preferably carried out under vacuum atmosphere at $10^{-5}$ Torr or less. Further, the above layer may be formed in an inert gas such as nitrogen, argon or helium gas.

The solvent used for forming each layer of the electrophotographic photoreceptor is selected from those solvents which do not affect the undercoat layer and other photosensitive layer. Specific examples of the solvent include aromatic hydrocarbons such as benzene and xylene, ketones such as Acetone, methyl ethyl ketone and cylcohexanone, alcohols such as methanol and ethanol, esters such as ethyl acetate and methyl cellosolve, halogenated aliphatic hydrocarbons such as carbon tetrachloride, chloroform, dichloromethane, dichloroethane and trichloroethylene, halogenated aromatic hydrocarbons such as chlorobenzene and dichlorobenzene, and ethers such as tetrahydrofuran and dioxane, while the above solvent shall not be limited to these.

The hole-transport layer is formed by applying the hole-transport material or a solution of the hole-transport material in a resin. The hole-transport material used for the photoreceptor of the present invention may be a combination of the compound of the formula (1) with other hole-transport material. The compound of the formula (1) is advantageous for improving the sensitivity and durability, since it has excellent compatibility with a resin so that a crystal is hardly precipitated.

For improving the electrophotographic properties and image properties, an undercoat layer may be provided between the substrate and the organic layer as required. The undercoat layer may be formed from resins such as polyamides, casein, polyvinyl alcohol, gelatin and polyvinyl butyral and metal oxides such as aluminum oxide.

The hole-transport material of the present invention can be suitably used not only as a hole-transport material for an organic EL device or an electrophotographic photoreceptor, but also as an organic photoconductive material for a photoelectric converter, a solar cell and an image sensor.

The present invention will be explained further in detail hereinafter with reference to Examples.

Synthesis of Compound (1)

17.4 Grams of 9,9-bis(4-aminophenyl)fluorene, 27.1 g of p-iodotoluene, 26.1 g of potassium hydroxide and 0.05 g of copper sulfate pentahydrate were placed in a flask and allowed to react under nitrogen atmosphere at 200° C. for 12 hours. Then, the reaction mixture was cooled to 60° C., diluted with ethyl acetate and filtered. The filtrate was concentrated under reduced pressure, and the residue was recrystallized from toluene to give 35.2 g of a crystal. The crystal was analyzed by mass spectrometry, infrared absorption spectrum and NMR spectrum to show that the crystal was Compound (1).

The result of elemental analysis of Compound (1) was as follows.

Result of elemental analysis.

As $C_{53}H_{44}N_2$

Calculated (%): C: 89.83, H: 6.22, N: 3.95

Found (%): C: 89.52, H: 6.47, N: 4.01

Figure 6:
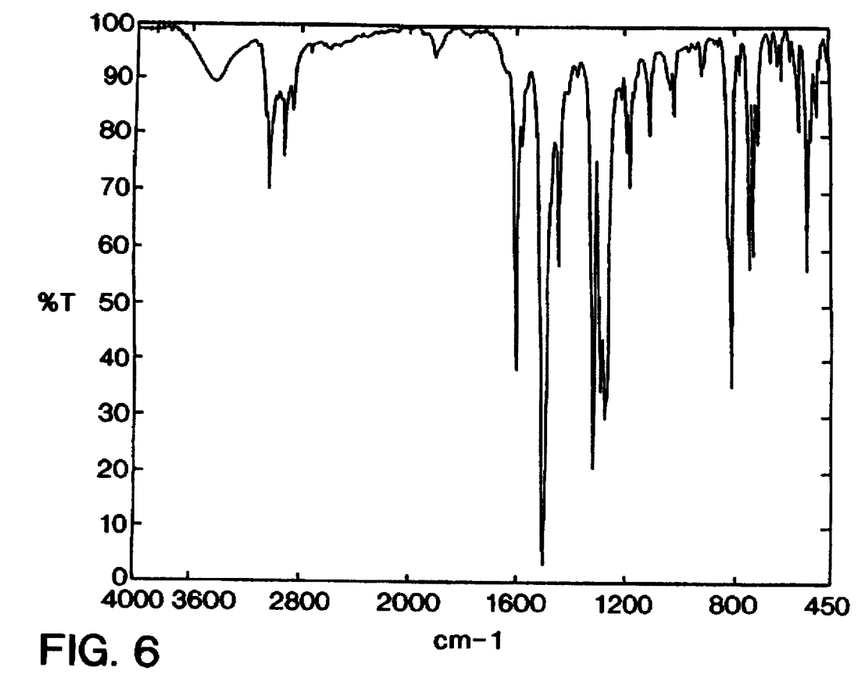
FIG. 6 is an infrared absorption spectrum of Compound (1).

FIG. 6 shows the infrared absorption spectrum of Compound (1) (KBr tablet method).

Synthesis of Compound (2)

34.8 Grams of 9,9-bis(4-aminophenyl)fluorene, 81.3 g of iodotoluene, 100 g of 1,3-dimethyl-2-imidazoldione, 78.3 g of potassium hydroxide and 0.1 g of cuprous chloride were placed in a flask and allowed to react under nitrogen atmosphere at 200° C. for 12 hours. Then, the reaction mixture was cooled to 60° C., diluted with ethyl acetate and filtered. The filtrate was concentrated under reduced pressure, and the residue was recrystallized from toluene to give 48.5 g of a crystal. The crystal was analyzed by mass spectrometry, infrared absorption spectrum and NMR spectrum to show that the crystal was Compound (2).

The result of elemental analysis of Compound (2) was as follows.

Result of elemental analysis

As $C_{53}H_{44}N_2$

Calculated (%): C: 89.83, H: 6.22, N: 3.95

Found (%): C: 89.68, H: 6.51, N: 3.81

Figure 7:
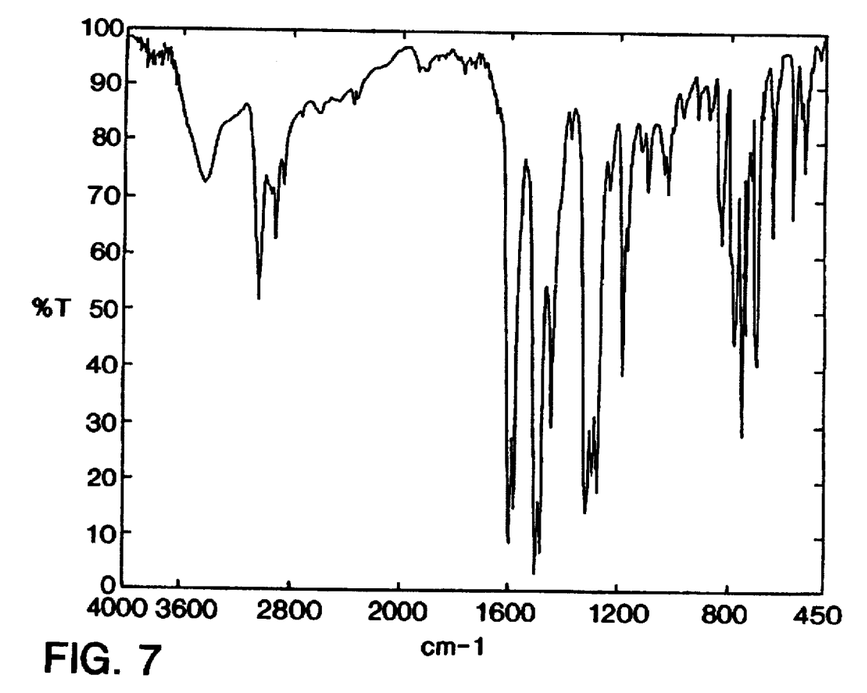
FIG. 7 is an infrared absorption spectrum of Compound (2).

FIG. 7 shows the infrared absorption spectrum of Compound (2) (KBr tablet method).

Measurement of light emission brightness

The light emission brightness was measured with a brightness measuring device "LS-110" supplied by Minolta Camera Co., Ltd., and the light emission efficiency is calculated by the following equation.

$$\eta(lm/W)=\pi L_0(cd/m^2)/P_{in}(W/m^2)$$

wherein:

$\eta$=light emission efficiency $L_0$=brightness $P_{in}$=input voltage

EXAMPLE 1

A light-emitting layer having a thickness of 500 angstroms Compound (1) was formed on a cleaned glass substrate with an ITO electrode thereon by a vacuum deposition method. The vacuum deposition was carried out under a vacuum of $10^{-6}$ Torr at a substrate temperature of room temperature. An electrode having a thickness of 1,500 angstroms was formed from a magnesium/silver (10/1) alloy on the light-emitting layer by a vapor deposition method to give an organic EL device as shown in FIG. 1. This device showed a light emission of 53 cd/m² at a direct current of 10V. The light emission efficiency thereof was 1.8 lm/W.

EXAMPLE 2

A dispersion of Compound (3) in chloroform was spin-coated on a cleaned glass substrate with an ITO electrode thereon to form a light-emitting layer having a thickness of 500 angstroms. An electrode having a thickness of 1,500 angstroms was formed from a magnesium/silver (10/1) alloy on the light-emitting layer by a vapor deposition method to give an organic EL device as shown in FIG. 1. This device showed a light emission of 42 cd/m$^2$ at a direct current of 10V. The light emission efficiency thereof was 1.2 lm/W.

EXAMPLE 3

A dispersion of Compound (5), N,N'-diphenyl-N,N'-(3-methylphenyl) -1,1'-biphenyl-4,4'-diamine and poly-N-vinylcarbazole (mixing ratio: 3:2:1) in chloroform was spin-coated on a cleaned glass substrate with an ITO electrode thereon to form a light-emitting layer having a thickness of 1,000 angstroms. An electrode having a thickness of 1,500 angstroms was formed from a magnesium/silver (10/1) alloy on the light-emitting layer by a vapor deposition method to give an organic EL device as shown in FIG. 1. This device showed a light emission of 130 cd/m$^2$ at a direct current of 10V. The light emission efficiency thereof was 2.0 lm/W.

EXAMPLE 4

N,N'-diphenyl-N,N'-(3-methylphenyl)-1,1'-biphenyl-4,4'-diamine was vacuum-deposited on a cleaned glass substrate with an ITO electrode thereon to form a hole-injecting layer having a thickness of 300 angstroms. Then, Compound (1) was vacuum-deposited to form a light-emitting layer having a thickness of 500 angstroms. An electrode having a thickness of 1,500 angstroms was formed from a magnesium/silver (10/1) alloy on the light-emitting layer by a vapor deposition method to give an organic EL device as shown in FIG. 2. In this case, the hole-injecting layer and the light-emitting layer were formed in a vacuum of 10$^{-6}$ Torr at a substrate temperature of room temperature. This device showed a light emission of about 200 cd/m$^2$ at a direct current of 10V. This result show that the compound of the present invention is a light-emitting substance which carries electrons. The light emission efficiency thereof was 2.7 lm/W.

EXAMPLE 5

Compound (1) was vacuum-deposited on a cleaned glass substrate with an ITO electrode to form a hole-injecting layer having a thickness of 300 angstroms. Then, a tris(8-hydroxyquinoline)aluminum complex was vacuum-deposited to form a light-emitting layer having a thickness of 500 angstroms. An electrode having a thickness of 1,500 angstroms was formed from a magnesium/silver (1.0/1) alloy on the light-emitting layer by a vapor deposition method to give an organic EL device as shown in FIG. 2. In this case, the hole-injecting layer and the light-emitting layer were formed in a vacuum of 10$^{-6}$ Torr at a substrate temperature of room temperature. This device showed a light emission of about 310 cd/m$^2$ at a direct current of 10V. The light emission efficiency thereof was 4.6 lm/W.

EXAMPLE 6

N,N'-diphenyl-N,N'-(3-methylphenyl)-1,1'-biphenyl-4,4'-diamine was vacuum-deposited on a cleaned glass substrate with an ITO electrode thereon to form a hole-injecting layer having a thickness of 300 angstroms. Then, Compound (6) was vacuum-deposited to form a light-emitting layer having a thickness of 200 angstroms. Further, [2-(4-tert-butylphenyl)-5-(biphenyl)-1,3,4-oxadiazole] was vacuum-deposited to form an electron-injecting layer having a thickness of 200 angstroms. An electrode having a thickness of 200 angstroms was formed from a magnesium/silver (10/1) alloy on the electron-injecting layer by a vapor deposition methods to give an organic EL device as shown in FIG. 8. This device showed a light emission of about 390 cd/m$^2$ at a direct current of 10V. The light emission efficiency thereof was 4.2 lm/W.

When all the organic EL devices obtained in Examples 1 to 6 were allowed to emit light continuously at 1 mA/cm$^2$, the light emission was stable for more than 1,000 hours.

The organic EL devices of the present invention show improvements in light emission efficiency, light emission brightness and device life, and impose no limitation on the light-emitting substance, the light-emitting auxiliary substance, the hole-transport material, the electron-transport material, the sensitizer, the resin and the material for the electrode, used in combination and the method of producing the device.

EXAMPLE 7

4 Grams of ε-type phthalocyanine, 2 g of Compound (2) and 14 g of a polyester resin (VYLON, 200 supplied by Toyobo Co., Ltd.) were dipsersed in 80 g of tetrahydrofuran with a ball mill for 5 hours. The resultant dispersion was applied to an aluminum substrate and dried to form a single-layered electrophotographic photoreceptor having a thickness of 20 μm as shown in FIG. 4.

EXAMPLE 8

6 Grams of dibromoanthanthrone, 2 g of Compound (6) and 12 g of a polyester resin (VYLON 200, supplied by Toyobo Co., Ltd.) were dispersed in 80 g of tetrahydrofuran with a ball mill for 5 hours. The resultant dispersion was applied to an aluminum substrate and dried to form a single-layered electrophotographic photoreceptor having a thickness of 20 μm as shown in FIG. 4.

EXAMPLE 9

2 Grams of τ-form phthalocyanine and 2 g of a polyvinyl butyral resin (BH-3, supplied by Sekisui Chemical Co., Ltd.) were dispersed in 96 g of tetrahydrofuran with a ball mill for 2 hours. The resultant dispersion was applied to an aluminum substrate and dried to form a charge-generating layer having a thickness of 0.3 μm. Then, 10 g of Compound (2) and 10 g of a polycarbonate resin (L-1250, supplied by Teijin Kasei K. K.) were dissolved in 80 g of dichloromethane, and the resultant solution was coated on the charge-generating layer and dried to form an electron-transport layer having a thickness of 20 μm so that a laminated electrophotographic photoreceptor as shown in FIG. 5 was formed.

EXAMPLE 10

2 Grams of N,N'-bis(2,6-dichlorophenyl)-3,4,9,10-perylenedicarboxyimide and 2 g of a polyvinyl butyral resin (BH-3, supplied by Sekisui Chemical Co., Ltd.) were dispersed in 96 g of tetrahydrofuran with a ball mill for 2 hours. The resultant dispersion was applied to an aluminum substrate and dried to form a charge-generating layer having a thickness of 0.3 μm. Then, 10 g of Compound (2) and 10 g of a polycarbonate resin (L-1250, supplied by Teijin Kasei K. K.) were dissolved in 80 g of dichloromethane, and the resultant solution was coated on the charge-generating layer and dried to form a hole-transport layer having a thickness of 20 μm, so that a laminated electrophotographic photoreceptor as shown in FIG. 5 was formed.

The electrophotographic photoreceptors obtained in Examples 7 to 10 were measured for electrophotographic properties by the following method.

Each electrophotographic photoreceptor was set in an electrostatic paper analyzer (EPA-8100, supplied by Kawaguchi Denki Seisakusho), and exposed to white light (5 lux) at a static mode of 2 at a corona charge of −5.2 KV to determine a ratio (dark decay ratio: $DDR_2=V_2/V_0$) between an initial surface potential ($V_0$) and a surface potential ($V_2$) after the photoreceptor was allowed to stand in a dark place for 2 seconds, a half exposure sensitivity ($E_{1/2}$) on the basis of a time during which the charge amount decreased to ½ of the initial charge amount, and a surface potential ($VR_3$) after 3 seconds from the optical exposure. Table 1 shows the electrophotographic properties of the electrophotographic photoreceptors obtained in Examples 7 to 10.

TABLE 1

| Example | $V_0$ (-V) | $DDR_2$ (%) | $E_{1/2}$ (lux · s) | $VR_3$ (-V) |
|---|---|---|---|---|
| 7 | 530 | 92 | 2.3 | 15 |
| 8 | 590 | 95 | 2.9 | 12 |
| 9 | 710 | 96 | 0.7 | 3 |
| 10 | 720 | 95 | 1.3 | 5 |

When the above exposure was repeated more than 10,000 times to measure each electrophotographic photoreceptor for electrophotographic properties, all the photoreceptors obtained in Examples 7 to 10 showed stable surface potentials and sensitivities.

The present invention provides compounds having excellent hole-transport capability. The compounds provided by the present invention show high light emission efficiency and high brightness as compared with conventional compounds, and give organic EL devices having longer device lives and electrophotographic photoreceptors which are excellent in initial electrophotographic properties such as sensitivity, hole-transport properties, initial surface potential and dark attenuation ratio and show less fatigue when used repeatedly.

What is claimed is:

1. A hole-transporting material of the formula (I)

wherein each of $R^1$ to $R^{10}$, $R^{12}$ to $R^{15}$, $R^{17}$ and $R^{18}$ is independently a hydrogen atom, a halogen atom, an alkyl group, a substituted alkyl group, an alkoxy group, a substituted alkoxy group, a thioalkoxy group, a substituted thioalkoxy group, a cyano group, an amino group, a monosubstituted amino group, a hydroxyl group, a mercapto group, an aryloxy group, a substituted aryloxy group, an arylthio group, a substituted arylthio group, a carbocyclic aromatic group, a substituted carbocyclic aromatic group, a heterocyclic aromatic group, a substituted heterocyclic aromatic group, a heterocyclic group or a substituted heterocyclic group, and any neighboring substituents may form an aliphatic cyclic group, a substituted aliphatic cyclic group, a carbocyclic aromatic group, a substituted carbocyclic aromatic group, a heterocyclic aromatic group, a substituted heterocyclic aromatic group, a heterocyclic group or a substituted heterocyclic group, and each of $R^{11}$ and $R^{16}$ is independently a disubstituted amino group selected from the group consisting of diphenylamino, ditolylamino, dimethoxyphenylamino, bis(p-(N,N-diphenyl)aminophenyl)amino and dithiophenylamino.

2. A hole-transporting material according to claim 1, wherein each of $R^{11}$ and $R^{16}$ is diphenylamino.

3. A hole-transporting material according to claim 1, wherein each of $R^{11}$ and $R^{16}$ is ditolylamino.

4. A hole-transporting material according to claim 3, wherein the ditolylamino is di-p-tolylamino.

* * * * *